(12) United States Patent
Park

(10) Patent No.: US 12,311,139 B2
(45) Date of Patent: May 27, 2025

(54) NEGATIVE POISSON'S RATIO MATERIALS FOR MEDICAL APPLICATIONS

(71) Applicant: Joon Bu Park, Las Vegas, NV (US)

(72) Inventor: Joon Bu Park, Las Vegas, NV (US)

( * ) Notice: Subject to any disclaimer, the term of this patent is extended or adjusted under 35 U.S.C. 154(b) by 894 days.

(21) Appl. No.: 17/398,426

(22) Filed: Aug. 10, 2021

(65) Prior Publication Data

US 2023/0048709 A1    Feb. 16, 2023

(51) Int. Cl.
| | | |
|---|---|---|
| *A61J 1/10* | (2006.01) | |
| *A61M 39/08* | (2006.01) | |
| *F16L 11/12* | (2006.01) | |
| *F16L 11/20* | (2006.01) | |
| *A61M 39/00* | (2006.01) | |
| *F16L 11/08* | (2006.01) | |

(52) U.S. Cl.
CPC ............. *A61M 39/08* (2013.01); *A61J 1/10* (2013.01); *F16L 11/12* (2013.01); *F16L 11/20* (2013.01); *A61M 2039/0009* (2013.01); *A61M 2207/00* (2013.01); *F16L 11/085* (2013.01)

(58) Field of Classification Search
CPC ....................................................... A61J 1/10
See application file for complete search history.

(56) References Cited

U.S. PATENT DOCUMENTS

| | | | |
|---|---|---|---|
| 5,487,739 A * | 1/1996 | Aebischer | ................ B01J 13/02 604/93.01 |
| 7,951,880 B2 | 5/2011 | Lim et al. | |
| 2003/0114917 A1 | 6/2003 | Holloway et al. | |
| 2006/0129227 A1 | 6/2006 | Hengelmolen | |
| 2007/0213838 A1 | 9/2007 | Hengelmolen | |
| 2010/0029789 A1 * | 2/2010 | Chen | ........................ A61P 43/00 514/777 |
| 2013/0344601 A1 | 12/2013 | Soman et al. | |
| 2018/0149300 A1 | 5/2018 | Weisenberg | |
| 2018/0243525 A1 * | 8/2018 | Virr | ..................... A61M 16/142 |

OTHER PUBLICATIONS

International Search Report and Written Opinion in International Applu. No. PCT/US2022/074711, dated Nov. 25, 2022, 10 pages.

(Continued)

*Primary Examiner* — Jessica Arble
(74) *Attorney, Agent, or Firm* — Fish & Richardson P.C.

(57) ABSTRACT

A medical device includes a multi-layer body defining an interior space configured to contain a liquid. The multi-layer body includes a solid outer wall having a positive Poisson's ratio and a porous inner wall having a negative Poisson's ratio. A method of making a multi-layer body includes applying a stimulus to a precursor material to cause the precursor material to form a porous wall having a negative Poisson's ratio, and attaching a solid wall to the porous wall to form the multi-layer body, the solid wall having a positive Poisson's ratio. A suture includes one or more filaments, at least a first filament of the one or more filaments including a negative Poisson's ratio material. A medical device includes a biocompatible hydrogel, and the biocompatible hydrogel includes a composite of a first material having a negative Poisson's ratio and a second material having a positive Poisson's ratio.

15 Claims, 14 Drawing Sheets

(56) References Cited

OTHER PUBLICATIONS

Calo et al., "Biomedical applications of hydrogels: A review of patents and commercial products," European Polymer Journal, Apr. 2015, 65: 252-267.
Choi et al., "Recent advances in photo-crosslinkable hydrogels for biomedical applications," BioTechniques, Jan. 2019, 66(1):40-53.
Cidade et al., "Injectable Hydrogels Based on Pluronic/Water Systems Filled with Alginate Microparticles for Biomedical Applications," Materials, Apr. 2019, 12(7): 1083, 13 pages.
Da Silva et al., "Do HEMA-free adhesive systems have better clinical performance than HEMA-containing systems in noncarious cervical lesions? A systematic review and meta-analysis," Journal of Dentistry, Jul. 2018, 74: 1-14.
De Vries et al., "Shrinkage influenced by chain rupture during tensile deformation," Journal of Macromolecular Science, Part B, 1978, 15(3): 409-420.
Dutta et al., "Temperature and pH responsive 3D printed scaffolds," Journal of Materials Chemistry B, Nov. 2017, 5(48): 9514-9521.
Fredericks et al., "Morphological and structural changes in a copolymer of glycolide and lactide occurring as a result of hydrolysis," Journal of Polymer Science: Polymer Physics Edition, Jan. 1984, 22(1):57-66.
Guerra et al., "Photopolymerizable Resins for 3D-Printing Solid-Cured Tissue Engineered Implants," Current Drug Targets, Jun. 2019, 20(8): 823-828.
Gungor-Ozkerim et al., "Bioinks for 3D bioprinting: an overview," Biomaterials Science, 2018, 6(5): 915-946.
Khang et al., "Prevention of platelet adhesion on polysulfone porous catheter by saline solution perfusion, II. Ex vivo and in vivo investigation," Bio-medical Materials and Engineering, 1996, 6(2): 123-134.
Khang et al., "Prevention of platelet adhesion on the polysulfone porous catheter by saline solution perfusion, I. In vitro investigation, " Bio-medical Materials and Engineering, 1996, 6(1):47-66.
Kim et al., "1—Biomedical nanomaterials in tissue engineering," Nanomaterials in Tissue Engineering, Fabrication and Application, Woodhead Publishing Series in Biomaterials, 2013, pp. 1-23, 24e-25e.
Kim et al., "Prevention of Blood Cell Adhesion in Porous Inner Wall of Double-Layered Tube by Saline Perfusion," Bio-medical Materials and Engineering, 1993, 3(2): 85-100.
Kim et al., "Prevention of Mural Thrombus in Porous Inner Tube of Double-Layered Tube by Saline Perfusion, " Bio-Medical materials and Engineering, 1993, 3(2): 101-116.
Kim et al., "Three-Dimensional Porous Biodegradable Polymeric Scaffolds Fabricated with Biodegradable Hydrogel Porogens," Tissue Engineering Part C: Methods, Apr. 2009, 15(4): 583-594.
Lee, "Injectable hydrogels delivering therapeutic agents for disease treatment and tissue engineering," Biomaterials Research, 2018, 22(1): 27, 14 pages.
Lim et al., "Novel method for treatment of discogenic low back pain using percutaneously injectable in-situ forming hydrogel," 52nd Annual Meeting of The Orthopedic Research Society, Mar. 5-8, 2006, Chicago, IL, 1 page.
Naito et al., "The advantages of three-dimensional culture in a collagen hydrogel for stem cell differentiation," Journal of Biomedical Materials Research Part A, Mar. 2013, 101(10): 2838-2845.
Park et al., "Chain Rupture during Tensile Deformation of Nylon 6 Fibers," Journal of Macromolecular Science, Part B, 1978, 15(2): 205-227.
Park et al., "Prevention of Mural Thrombus in Porous Inner Tube of Double-Layered Tube by Saline Perfusion," Bio-medical Materials and Engineering, 1993, 3(2): 101-116.
Park et al., "Structure changes caused by strain annealing of nylon 6 fibers," Journal of Macromolecular Science, Part B, 1978, 15(2): 229-256.
Zaragoza et al., "Exploring the Role of Nanoparticles in Enhancing Mechanical Properties of Hydrogel Nanocomposites," Nanomaterials, Oct. 2018, 8(11): 882, 10 pages.
International Preliminary Report on Patentability in International Appln. No. PCT/US2022/074711, mailed on Feb. 22, 2024, 8 pages.

\* cited by examiner

NEGATIVE POISSON'S RATIO MATERIALS FOR MEDICAL APPLICATIONS

BACKGROUND

The present disclosure relates generally to materials for and construction of various types of medical devices and implants, including blood-contacting devices (e.g., dialysis tubes) and breast implants.

Medical devices and implants can be used during medical procedures and/or integrated into patients' bodies for various purposes, including transporting fluids in or out of the body, replacing a missing biological structure, supporting a damaged biological structure, or enhancing an existing biological structure.

SUMMARY

We describe here medical devices and implants, such as dialysis tubes, sutures, and biocompatible polymer implants, that include materials having a negative Poisson's ratio ("NPR materials"). For instance, a blood-contacting surface may be formed of a porous NPR material so as to permit the perfusion of water through the surface while providing improved deformation properties. Medical devices and implants incorporating NPR materials can be lighter, more resilient, and more mechanically stable than devices and implants without NPR materials, and can provide improved homeostasis.

One aspect of this disclosure describes a medical device. The medical device includes a multi-layer body defining an interior space configured to contain a liquid. The multi-layer body includes a solid outer wall having a positive Poisson's ratio, and a porous inner wall having a negative Poisson's ratio.

This medical device, and at least some other medical devices described herein, may have any one or more of at least the following characteristics.

In some implementations, the medical device includes a hydrogel layer on an inner surface of the porous inner wall.

In some implementations, the hydrogel layer has a negative Poisson's ratio.

In some implementations, the solid outer wall and the porous inner wall are arranged to permit perfusion of a second liquid from between the solid outer wall and the porous inner wall and through the porous inner wall into the interior space.

In some implementations, the medical device includes a port through which the second liquid can be introduced to perfuse through the porous inner wall into the interior space.

In some implementations, the medical device includes a blood bag, and the multi-layer body forms a wall of the blood bag.

In some implementations, the solid outer wall forms an outer tube, and the porous inner wall forms an inner tube arranged coaxially within the outer tube.

In some implementations, the medical device includes a catheter, and the outer tube and the inner tube form a catheter tube configured for flow of the liquid through the inner tube.

In some implementations, the liquid includes blood.

In some implementations, the porous inner wall has an interconnected porous structure.

In some implementations, the multi-layer body includes a plurality of solid outer walls, each of the plurality of solid outer walls having a positive Poisson's ratio.

In some implementations, each of the porous inner wall and the solid outer wall has a thickness between 1 µm and 100 µm.

An aspect of this disclosure describes a method of making a multi-layer body. In the method, a stimulus is applied to a precursor material to cause the precursor material to form a porous wall having a negative Poisson's ratio. A solid wall is attached to the porous wall to form the multi-layer body, the solid wall having a positive Poisson's ratio. The multi-layer body is configured to contact liquid in a medical device.

This method, and at least some other methods described herein, may have any one or more of at least the following characteristics.

In some implementations, the stimulus includes at least one of heat or pressure.

In some implementations, the method includes applying a hydrogel on a first surface of the porous wall. The first surface is opposite a second surface of the porous wall to which the solid wall is attached.

In some implementations, the hydrogel has a negative Poisson's ratio.

In some implementations, the solid wall forms an outer tube, and the porous wall forms an inner tube arranged coaxially within the outer tube.

In some implementations, each of the porous wall and the solid wall has a thickness between 1 µm and 100 µm.

In some implementations, the solid wall and the porous wall are arranged to permit perfusion of a second liquid from between the solid wall and the porous wall and through the porous wall.

In some implementations, the multi-layer body defines an interior space. The porous wall is an inner wall with respect to the interior space, and the solid wall is an outer wall with respect to the interior space.

An aspect of this disclosure describes a suture. The suture includes one or more filaments, at least a first filament of the one or more filaments including a negative Poisson's ratio material.

This suture, and at least some other sutures described herein, may have any one or more of at least the following characteristics.

In some implementations, the first filament includes a core of the negative Poisson's ratio material, and a coating over the core, the coating having a positive Poisson's ratio.

In some implementations, the first filament includes a composite of the negative Poisson's ratio material and a positive Poisson's ratio material.

In some implementations, the composite includes a matrix composite.

In some implementations, the one or more filaments include a second filament braided with the first filament. The second filament includes a positive Poisson's ratio material.

In some implementations, the suture has a thickness between 1 µm and 1 mm.

In some implementations, the negative Poisson's ratio material includes at least one of polyglycolic acid, polylactide, polyethylene, polypropylene, a nylon, or a polyester.

An aspect of this disclosure describes a method of making a suture. The method includes providing a first filament having a negative Poisson's ratio, and coating the first filament in a coating having a positive Poisson's ratio. The suture includes the first filament coated with the coating.

This method, and at least some other methods described herein, may have any one or more of at least the following characteristics.

In some implementations, the first filament includes at least one of polyglycolic acid, polylactide, polyethylene, polypropylene, a nylon, or a polyester.

In some implementations, the method includes braiding a plurality of other filaments together with the first filament, to form the suture.

In some implementations, the suture has a thickness between 1 μm and 1 mm.

In some implementations, coating the first filament includes at least one of immersing the first filament, dip coating the first filament, spray coating the first filament, or depositing the coating by vapor deposition.

An aspect of this disclosure describes a method of making a suture. The method includes providing a first filament having a negative Poisson's ratio, providing a second filament having a positive Poisson's ratio, and braiding together the first filament and the second filament. The suture includes the first filament braided together with the second filament.

This method, and at least some other methods described herein, may have any one or more of at least the following characteristics.

In some implementations, the first filament includes at least one of polyglycolic acid, polylactide, polyethylene, polypropylene, a nylon, or a polyester.

In some implementations, the suture has a thickness between 1 μm and 1 mm.

In some implementations, the first filament includes a matrix composite of a negative Poisson's ratio material with a positive Poisson's ratio material.

An aspect of this disclosure describes another medical device. The medical device includes a biocompatible hydrogel. The biocompatible hydrogel includes a composite of a first material having a negative Poisson's ratio and a second material having a positive Poisson's ratio.

This medical device, and at least some other medical devices described herein, may include any one or more of at least the following characteristics.

In some implementations, the biocompatible hydrogel includes a first layer of the first material, and a second layer of the second material, the second layer coating the first layer.

In some implementations, the composite includes a matrix composite. In the matrix composite, the first material is a matrix phase and the second material is a reinforcement phase.

In some implementations, the composite includes a matrix composite. In the matrix composite, the second material is a matrix phase and the first material is a reinforcement phase.

In some implementations, the first material includes at least one of a silicone-based hydrogel or poly(2-hydroxyethyl methacrylate).

In some implementations, the medical device includes a contact lens. The contact lens includes the biocompatible hydrogel.

In some implementations, the medical device includes a breast implant. The biocompatible hydrogel forms a filler material of the breast implant.

An aspect of this disclosure describes a method of making a medical device. The method includes applying a stimulus to a precursor hydrogel material having a positive Poisson's ratio, the stimulus causing the precursor hydrogel material to become a second hydrogel material having a negative Poisson's ratio. The medical device includes the second hydrogel material.

This method of making a medical device, and at least some other methods of making medical devices described herein, may have any one or more of at least the following characteristics.

In some implementations, the stimulus includes at least one of heat or pressure.

In some implementations, the method includes applying a third hydrogel material as a coating on the second hydrogel material, the third hydrogel material having a negative Poisson's ratio.

In some implementations, the method includes forming a matrix composite of the second hydrogel material and a third hydrogel material. The third hydrogel material has a positive Poisson's ratio.

In some implementations, in the matrix composite, the second material is a matrix phase and the third material is a reinforcement phase.

In some implementations, in the matrix composite, the third material is a matrix phase and the second material is a reinforcement phase.

In some implementations, the second hydrogel material includes at least one of a silicone-based hydrogel or poly (2-hydroxyethyl methacrylate).

In some implementations, the medical device includes a contact lens.

In some implementations, the medical device includes a breast implant, and the second hydrogel material forms a filler material of the breast implant.

An aspect of this disclosure describes a dialyzer. The dialyzer includes an enclosure and a bundle of hollow tubular fibers encased by the enclosure. Each hollow tubular fiber of the bundle of hollow tubular fibers includes a porous inner wall having a negative Poisson's ratio, the porous inner wall defining an interior space configured to contain blood.

This dialyzer, and at least some other dialyzers describes herein, may have any one or more of at least the following characteristics.

In some implementations, each hollow tubular fiber includes a porous outer wall having a positive Poisson's ratio, the porous outer wall enclosing the porous inner wall of the hollow tubular fiber.

In some implementations, the dialyzer includes a hydrogel layer on an inner surface of the porous inner wall.

In some implementations, the hydrogel layer has a negative Poisson's ratio.

In some implementations, the porous inner wall of each hollow tubular fiber has an interconnected porous structure.

In some implementations, the porous inner wall has a thickness between 1 μm and 100 μm.

Other implementations are also within the scope of the claims.

DETAILED DESCRIPTION

We describe here medical devices and implants, such as blood-contacting membranes and biocompatible polymer implants, that are formed of materials having a negative Poisson's ratio ("NPR materials," also referred to as auxetic materials). These materials exist in contrast to positive Poisson's ratio (PPR) materials. For instance, sutures, catheters, dialysis tubes, blood-contacting surfaces, and medical implants can be formed partially or entirely of an NPR material. This composition can facilitate reduced weight, improved stress/strain responses that maintain homeostasis and device performance, and improved pliability, among other possible advantages.

Referring to FIGS. 1-4, several types of medical devices and implants are shown, including a kidney dialysis system 100, a catheter 200, breast implants 300, 310 and sutures 400. These medical devices and implants are non-limiting examples of the types, shapes, and sizes of medical devices and implants in which the NPR materials described here can be integrated.

Figure 1:
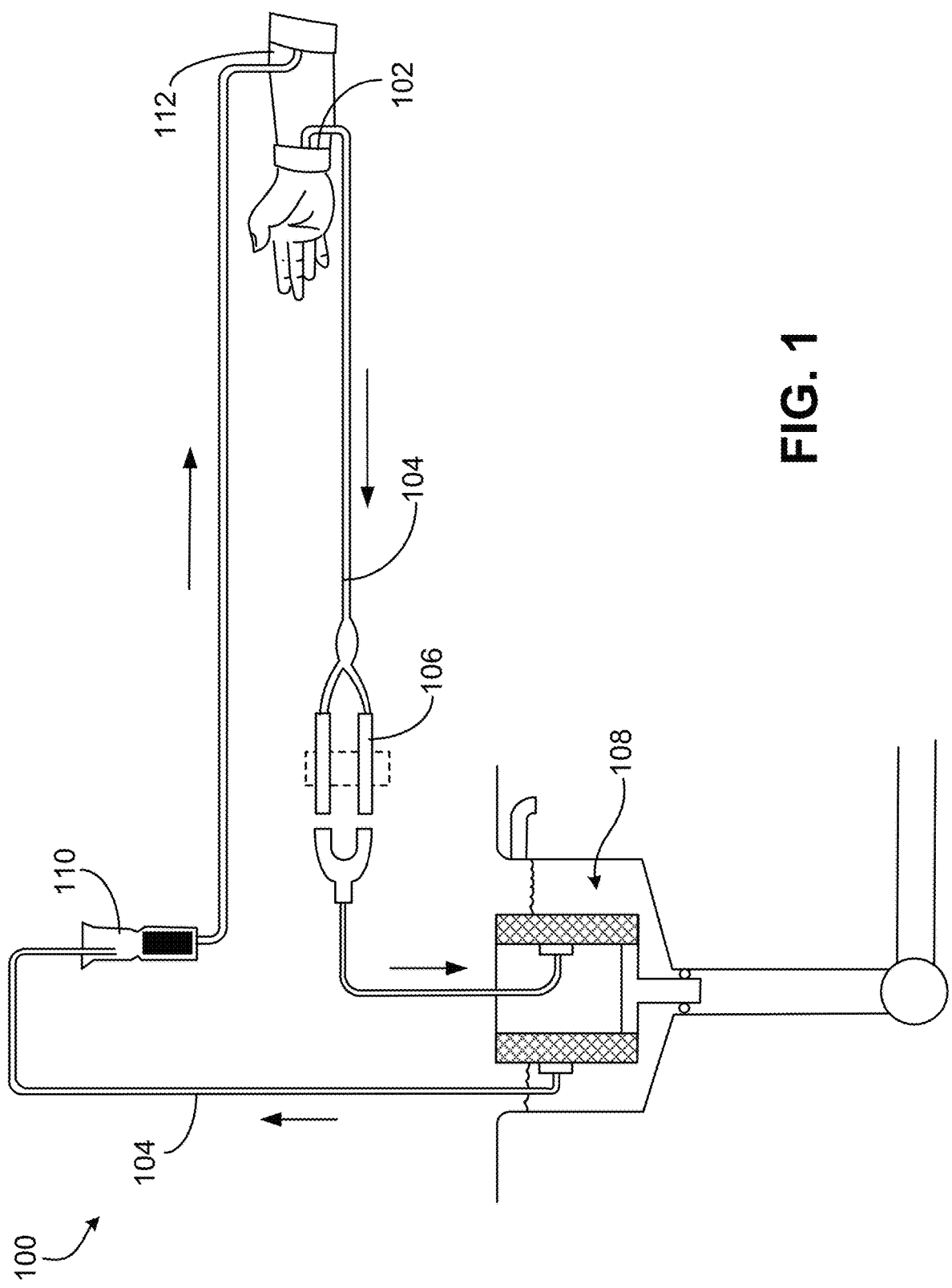
FIG. 1 is a diagram of an example dialysis system.

As shown in FIG. 1, in an example kidney dialysis system 100, blood is carried from an artery 102 through tubing 104. Driven by a pump 106, the blood is carried through a dialyzing module 108 in which the blood is purified, e.g., by the removal of uremic toxins. Carried by further tubing 104, the blood passes through a bubble trap 110 and is returned to a vein 112.

Circulation of the blood through the kidney dialysis system 100 (e.g., through the tubing 104) can cause damage to the blood over time. For example, direct contact between blood cells and the tubing 104 can damage blood cells, causing their rupture or deformation. However, this potentially harmful contact can be reduced by the incorporation of porous NPR material into the tubing 104 as an inner coaxial tube, as described in further detail below.

Figure 2:
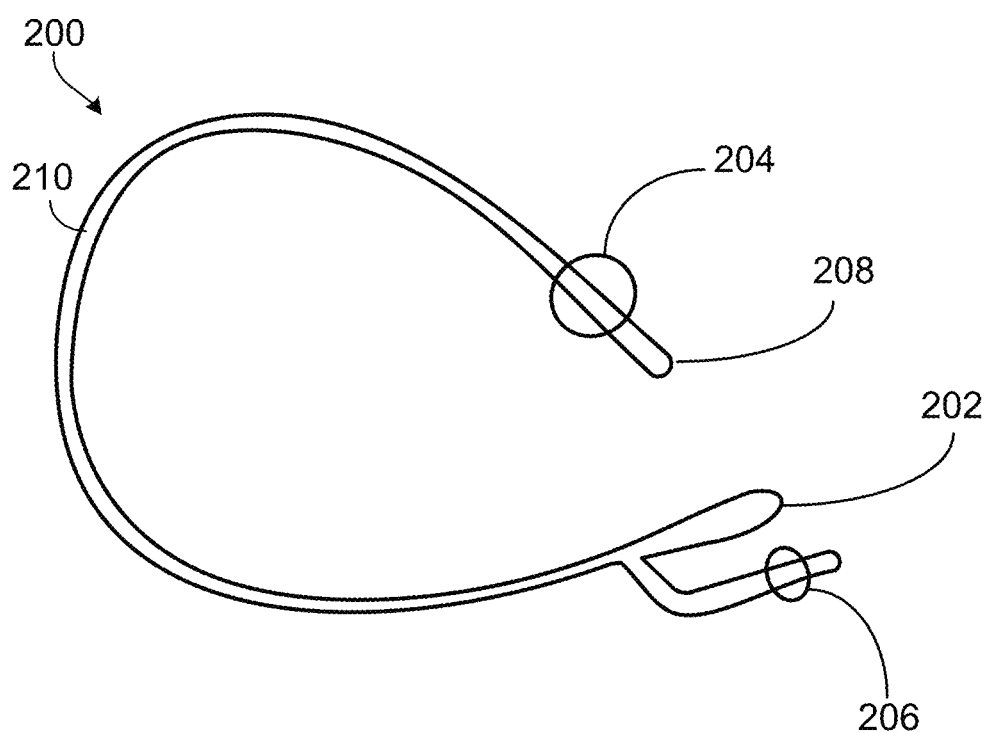
FIG. 2 is a diagram of an example catheter.

Catheters are tubes that can be inserted into the human body to serve various functions. As shown in FIG. 2, an example catheter 200 includes a first port 202 that receives fluid from a patient's body, provides fluid into the patient's body, or both. An optional balloon 204 can be inflated and deflated via a balloon port 206 to allow for positioning and removal of the catheter 200. A second port 208 serves to provide fluid to or drain fluid from the catheter 200. Tubing 210 joins the first port 202 and the second port 208. Some catheters are short-term catheters used during surgery, e.g., to administer drugs, drain fluids, or provide access to surgical instruments. Some catheters ("indwelling catheters") are designed for longer-term use, for example, as urinary catheters or peripherally inserted central catheters.

As described for the tubing 104 of FIG. 1, in some cases it may be desirable to limit direct contact between the fluid flowing through the catheter 200 and an inner surface of the catheter 200. For example, blood cells or platelets may be damaged by direct contact with an inner surface of the tubing 210. The use of porous NPR material as a liquid-perfused inner surface can reduce this contact and thereby reduce cell damage.

Figure 3A:
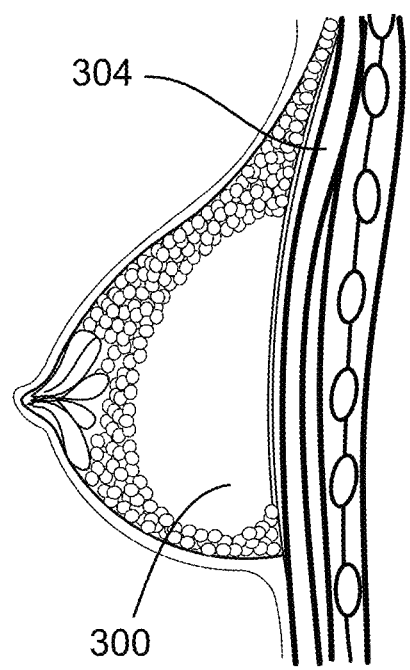
FIGS. 3A-3B are diagrams of example breast implants.
Figure 3B:
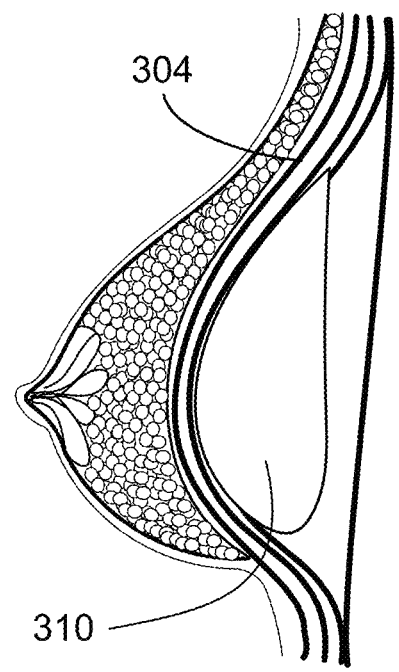

As shown in FIGS. 3A-3B, breast implants 300, 310 are placed within breast tissue 302 for reconstructive and/or cosmetic purposes. Breast implants 300 may be placed either in front of pectoral muscle 304, as in FIG. 3A, or behind pectoral muscle 304, as in FIG. 3B. Breast implants are often formed of polymers, such as silicone or poly(2-hydroxyethyl methacrylate) (pHEMA). pHEMA and some forms of silicone are hydrogel materials, meaning that they are crosslinked hydrophilic polymers that do not dissolve in water and that exhibit water-absorbing properties. pHEMA and some other polymers form hydrogels when hydrated (e.g., when in water); this disclosure uses "hydrogel" or "hydrogel material" to refer both to materials that exist as hydrogels in their pristine state and to materials that form hydrogels when hydrated, such as pHEMA.

Hydrogel materials can be caused to have a negative Poisson's ratio. When incorporated into breast implants, contact lenses, and other medical implants and devices, NPR hydrogels can provide a reduced implant weight. In addition, NPR hydrogels or composite NPR-PPR hydrogels may respond to stress and strain in ways that are more favorable than PPR-only hydrogels, e.g., NPR or NPR-PPR hydrogels may be less likely to rupture or damage surrounding tissue.

Figure 4:
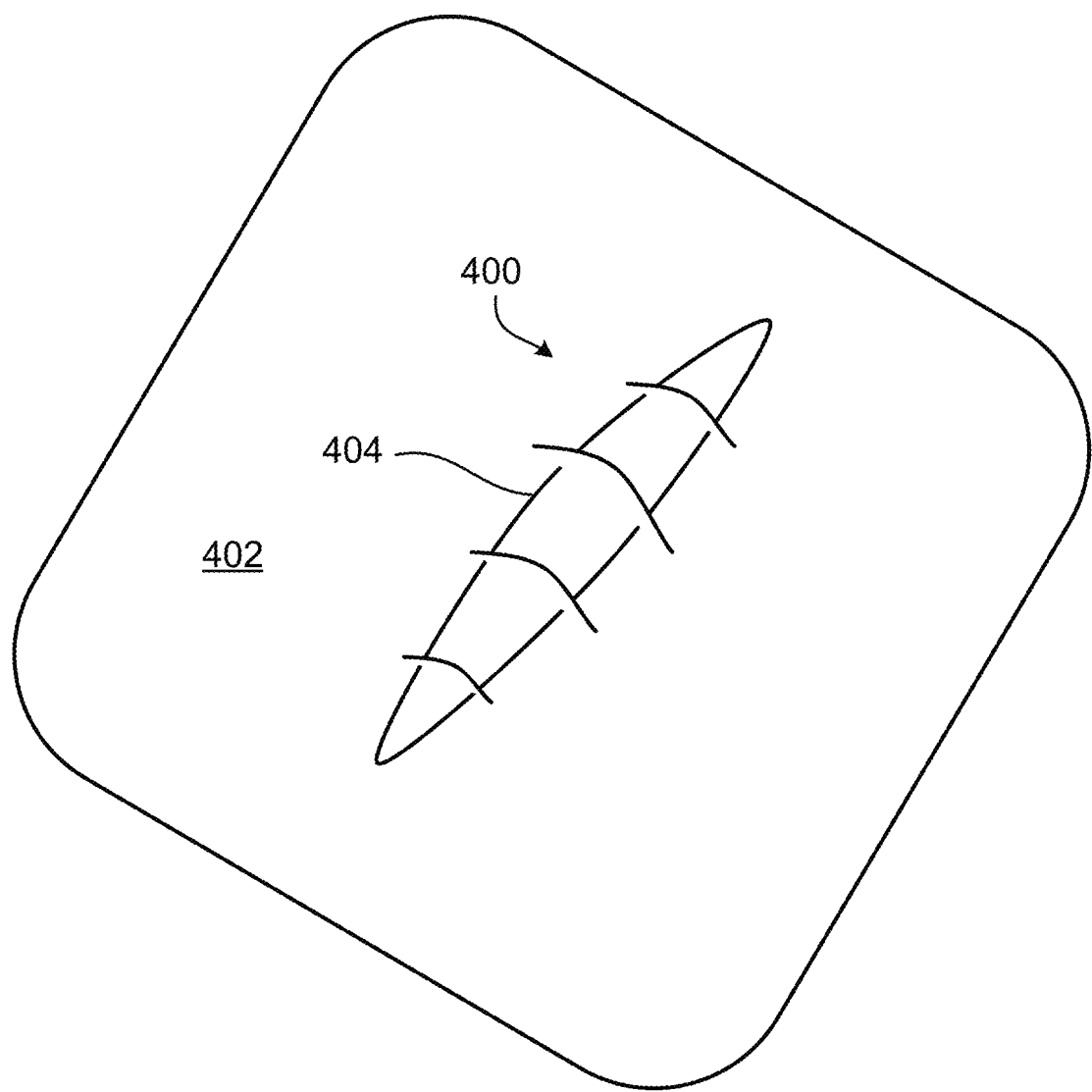
FIG. 4 is a diagram of an example suture.

As shown in FIG. 4, sutures 400 are threads used to hold together tissue 402, e.g., in the presence of an incision or wound 404. While silk or catgut sutures are sometimes used, most modern sutures are synthetic. For example, common suture materials include polymers such as polyglycolic acid (PGA), polylactide (PLA), polypropylene, nylons, polyesters, or co-polymers including at least one of these materials. However, in some cases, PPR sutures can be too heavy, can shrink or expand unfavorably when stretched or released, and/or can have too-low pliabilities. NPR sutures or composite NPR-PPR sutures can provide reduced weight, improved stress and strain characteristics, and increased pliability.

An NPR material is a material that has a Poisson's ratio that is less than zero, such that when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis). By contrast, a material with a positive Poisson's ratio (a "PPR material") has a Poisson's ratio that is greater than zero. When a PPR material experiences a positive strain along one axis (e.g., when the material is stretched), the strain in the material along the two perpendicular axes is negative (e.g., the material compresses in cross-section), and vice versa.

Figure 5:
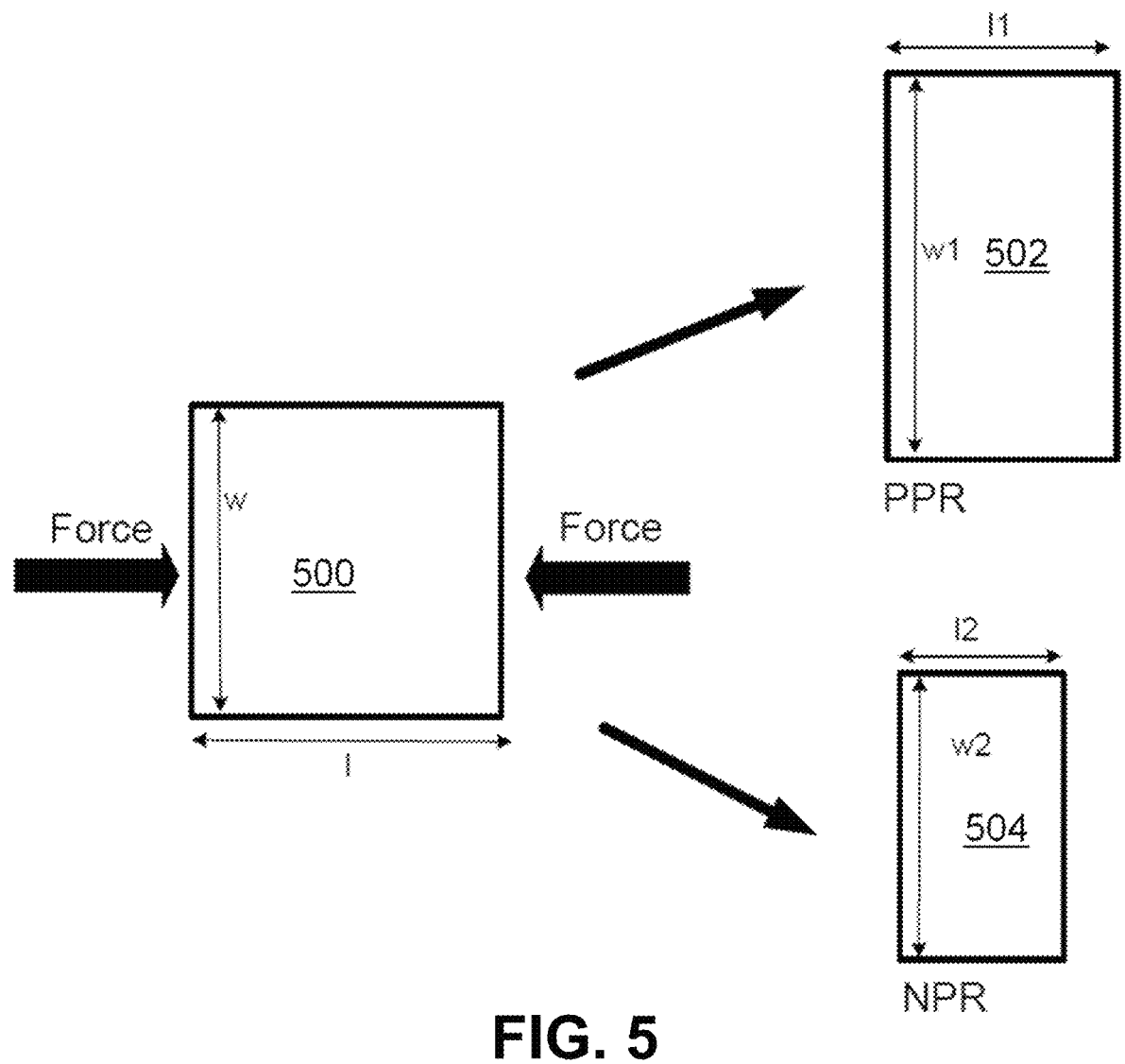
FIG. 5 is a diagram of an example NPR material.

Materials with negative and positive Poisson's ratios are illustrated in FIG. 5, which depicts a hypothetical two-dimensional block of material 500 with length l and width w.

If the hypothetical block of material 500 is a PPR material, when the block of material 500 is compressed along its width w, the material deforms into the shape shown as block 502. The width w1 of block 502 is less than the width w of block of material 500, and the length l1 of block 502 is greater than the length l of block of material 500: the material compresses along its width and expands along its length.

By contrast, if the hypothetical block of material 500 is an NPR material, when the block of material 500 is compressed along its width w, the material deforms into the shape shown as block 504. Both the width w2 and the length l2 of block 504 are less than the width w and length l, respectively, of block of material 500: the material compresses along both its width and its length.

NPR materials for integration into medical devices and implants can be foams, such as polymeric foams, ceramic foams, metallic foams, or combinations thereof. A foam is a multi-phase composite material in which one phase is gaseous and the one or more other phases are solid (e.g., polymeric, ceramic, or metallic). Foams can be closed-cell foams, in which each gaseous cell is sealed by solid material; open-cell foams, in which the each cell communicates with the outside atmosphere; or mixed, in which some cells are closed and some cells are open. NPR materials can be hydrogels, in some implementations formed of NPR foams.

An example of an NPR foam structure is a re-entrant structure, which is a foam in which the walls of the cells are concave, e.g., protruding inwards toward the interior of the cells. In a re-entrant foam, compression applied to opposing walls of a cell will cause the four other, inwardly directed walls of the cell to buckle inward further, causing the material in cross-section to compress, such that a compression occurs in all directions. Similarly, tension applied to opposing walls of a cell will cause the four other, inwardly directed walls of the cell to unfold, causing the material in cross-section to expand, such that expansion occurs in all directions. NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be polydisperse (e.g., the cells of the foam are not all of the same size) and disordered (e.g., the cells of the foam are randomly arranged, as opposed to being arranged in a regular lattice). An NPR foam can have a characteristic dimension (e.g., the size of a representative cell, such as the width of the cell from one wall to the opposing wall) ranging from 0.01 µm to about 3 mm, e.g., about 0.01 µm, about 0.05 µm, about 0.1 µm, about 0.5 µm, about 1 µm, about 10 µm, about 50 µm, about 100 µm, about 500 µm, about 1 mm, about 2 mm, or about 3 mm.

Examples of polymeric structures (e.g., foams) for integration into medical devices and implants include thermoplastic polymer foams (e.g., polyester polyurethane or polyether polyurethane); viscoelastic elastomer foams; or thermosetting polymer foams such as silicone rubber. Examples of metallic foams include metallic foams based on steel (e.g., stainless steel), copper, aluminum, titanium (e.g., $Ti_6Al_4V$, TiNbZr, or unalloyed titanium), or other metals, or alloys thereof, or ceramics composed of a metal oxide (e.g., aluminum oxide, titanium oxide, or zirconium oxide).

NPR-PPR composite materials are composites that include both regions of NPR material and regions of PPR material. NPR-PPR composite materials can be laminar composites, matrix composites (e.g., metal matrix composites, polymer matrix composites, or ceramic matrix composites), particulate reinforced composites, fiber reinforced composites, or other types of composite materials. In some examples, the NPR material is the matrix phase of the composite and the PPR material is the reinforcement phase, e.g., the particulate phase or fiber phase. In some examples, the PPR material is the matrix phase of the composite and the NPR material is the reinforcement phase. The reinforcement phase may be added to the already-formed matrix phase, or another method (e.g., a joint co-additive fabrication method) may be used.

Figure 6A:
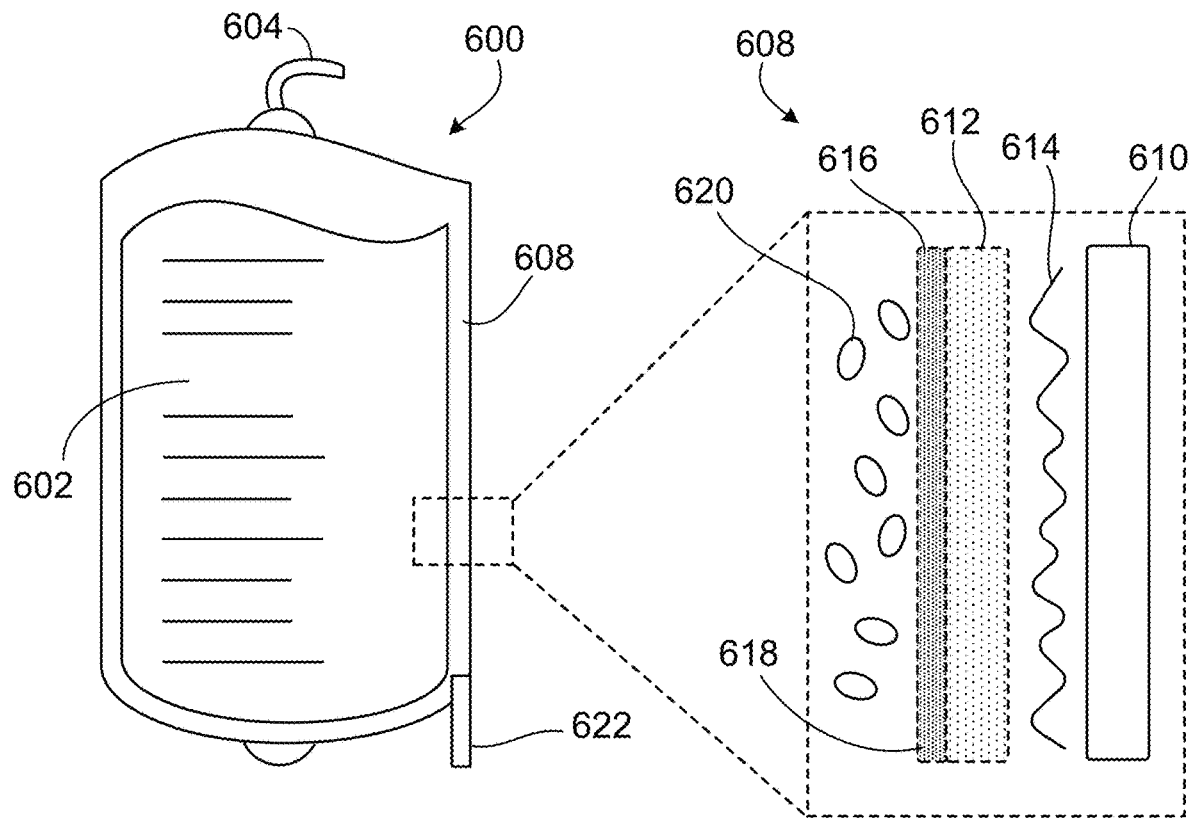
FIGS. 6A-6B are diagrams of example sidewalls.

Integration of NPR materials into medical devices and implants can take various forms. In some implementations, an NPR material is used to make a porous membrane in a blood-contacting device. For example, as shown in FIG. 6A, a blood bag 600 includes sidewalls 608 bounding an interior containing blood 602. One or more ports, inlets, and/or outlets 604 allow for the blood 602 to be directed into and/or out of the blood bag 600. The ports, inlets, and/or outlets 604 can also allow liquids to be directed into and/or out of a multi-layer membrane structure, as described in further detail below.

The blood 602 can be damaged during storage in the blood bag 600. For example, hemolysis, or the rupturing of red blood cells, can occur as a result of contact between the red blood cells and the sidewalls 608. Such direct contract can also damage other formed elements in the blood 602, such as white blood cells, platelets, and other plasma cells.

In some cases, this damage can be reduced or eliminated by incorporating a multi-layer structure into the sidewall 608. As shown in FIG. 6A, in some implementations, the sidewall 608 includes a solid outer membrane 610 and a porous inner membrane 612. The solid outer membrane 610 has a positive Poisson's ratio, while the porous inner membrane 612 has a negative Poisson's ratio. In the example of FIG. 6A, a hydrogel 616 further coats an inner surface of the porous inner membrane 612; however, in some implementations, the hydrogel 616 is not included.

During operation, a liquid 614 such as water (e.g., saline) is provided between the solid outer membrane 610 and the porous inner membrane 612. The porosity of the porous inner membrane 612 allows the liquid 614 to perfuse through the porous inner membrane 612 and wet an inner surface of the sidewall 608. In this example, the inner surface of the sidewall 608 is an inner surface 618 of the hydrogel 616. In implementations without an inner hydrogel, the inner surface of the sidewall 608 is an inner surface of the porous inner membrane 612 itself. In some implementations, the liquid 614 is provided at a positive pressure compared to the interior of the blood bag 600 in order to promote perfusion. The wetting of the inner surface 618 by the liquid 614 can reduce direct contact between blood cells 620 of the blood 602 and the inner surface 618, thereby reducing damage to the blood cells 620.

The hydrogel 616 can improve (e.g., increase) the wettability of the sidewall 608, thereby further decreasing the likelihood that blood cells 620 will contact or adhere to the sidewall 608. Various types of hydrogel 616 can be used as the inner coating. For example, the hydrogel 616 can be derived from a naturally-occurring material such as an olysaccharide (e.g., cellulose) and/or from a synthetic polymer such as a polypeptide, a polyester, or a polyphosphazene. For example, the hydrogel 616 may be pHEMA. In some implementations, the hydrogel 616 itself has a negative Poisson's ratio. Because the hydrogel 616 forms a layer on the porous inner membrane 612, which has a negative Poisson's ratio, an NPR hydrogel 616 can provide improved mechanical features (e.g., increased durability) because the NPR hydrogel 616 will deform similarly to the NPR porous inner membrane 612 when subjected to pressures and stresses.

The porous inner membrane 612 has a negative Poisson's ratio and, structurally, has an interconnected open porosity, the open porosity allowing the liquid 614 to perfuse therethrough. For example, the porous inner membrane 612 may include an NPR foam having a cellular and re-entrant and/or polydisperse structure, as described. The particular NPR material(s) making up the porous inner membrane 612 may be any of the NPR materials described in this disclosure, e.g., polymeric structures. The PPR material(s) making up the solid outer membrane 610 can likewise include polymers, plastics, or other materials, or a combination thereof, such as polyethylene and/or polyamide. Each of the solid outer membrane 610 and the porous inner membrane 612 may have a thickness between 1 μm and 500 μm, such as between 1 μm and 100 μm, between 10 μm and 250 μm, between 10 μm and 150 μm, between 10 μm and 100 μm, between 20 μm and 100 μm, or another thickness.

To facilitate introduction of the liquid 614 into the sidewall 608, the blood bag 600 may include one or more ports 622 fluidically coupled to the internal volume of the sidewall 608. A pump can be coupled to these ports 622 to maintain positive pressure inside the sidewall 608. The pressure can be selected so as to promote perfusion of the liquid 614 and reduce back-flow of the blood 602 into the sidewall 608 without causing excessive outflow of the liquid 614 into the internal space of the blood bag 600, which may dilute the blood 602. For example, the pressure can be selected such that approximate equilibrium is maintained with the liquid 614 wetting the internal surface of the sidewall 608 and only small amounts of, or no, substantial continued flow of the liquid 614 into the internal space of the blood bag 600.

There may be, but need not be, a well-defined space between the solid outer membrane 610 and the porous inner membrane 612 for the liquid 614. Rather, in some implementations, the solid outer membrane 610 and the porous inner membrane 612 directly abut one another, and the liquid 614 can be introduced so as to diffuse through the porous inner membrane 612 along the length of the interface between the porous inner membrane 612 and the solid outer membrane 610. For example, the solid outer membrane 610 and the porous inner membrane 612 may be bonded to one another or otherwise attached to one another. In some implementations, the solid outer membrane 610 and the porous inner membrane 612 are attached to one another at multiple attachment points and are spaced apart from one another between the attachment points.

Figure 6B:
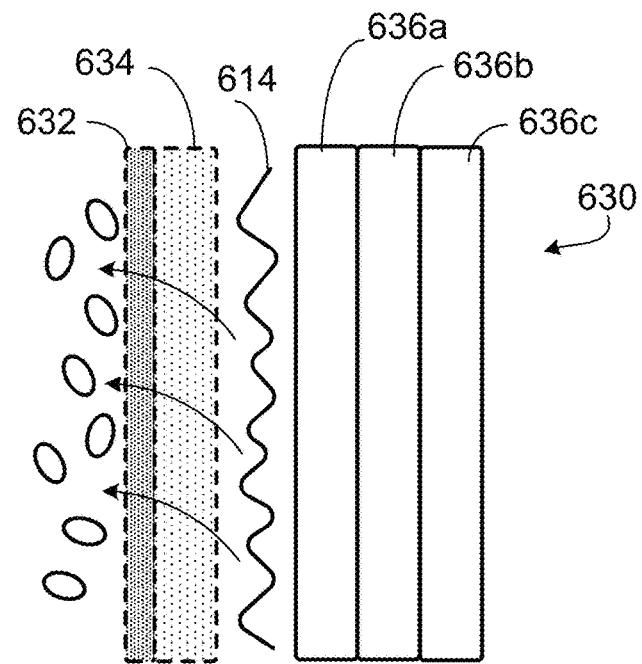

In some implementations, a sidewall including a porous inner NPR membrane includes more than two layers. For example, as shown in FIG. 6B, in some implementations a sidewall 630 includes a hydrogel layer 632, a porous NPR membrane 634, and two or more solid PPR layers 636a, 636b, 636c. The two or more solid PPR layers 636a, 636b, 636c may together promote improved flexibility, resilience, and chemical isolation compared to sidewalls with single PPR outer layers. In some implementations, one or more membrane layers besides the innermost membrane layer have a negative Poisson's ratio, in addition to the inner membrane layer.

The negative Poisson's ratio of the porous inner membrane 612 can provide various benefits. First, the structure of the NPR porous inner membrane is conducive to liquid perfusion and surface wetting. Second, in some implementations, the sidewall 608 containing the NPR porous inner membrane has more favorable mechanical responses to pressure and stress than PPR-only sidewalls. For example, the sidewall 608 may be less like to substantially deform and/or rupture than PPR-only sidewalls.

The design of the sidewall 608 may also be used for devices intended to contact materials besides blood. For example, a multi-layer sidewall incorporating an NPR porous inner membrane may be used in scientific research applications to reduce damage to liquid samples in contact with the sidewall, or may be used in medical applications for contact with liquid besides blood.

Figure 7A:
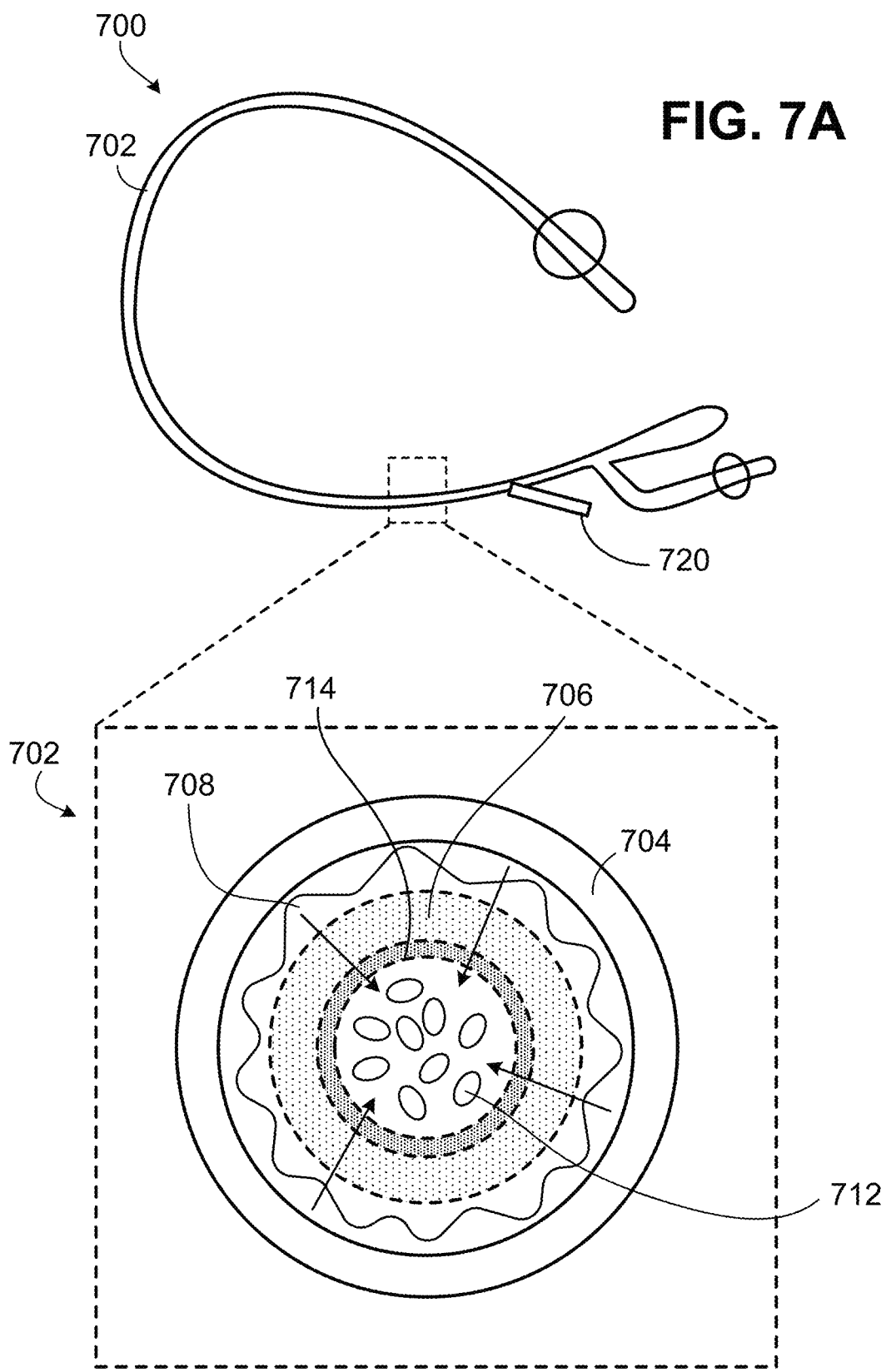
FIGS. 7A-7B are diagrams of example tubes.

The design of the sidewall 608 can be extended to NPR material-containing tubes usable in medical and other applications. As shown in FIG. 7A, a catheter 700 includes tubing 702. The tubing 702, shown in cross-section, includes a solid outer tube 704 having a positive Poisson's ratio and a porous inner tube 706 having a negative Poisson's ratio. The porous inner tube 706 extends coaxially inside the solid outer tube 704 such that liquid 708 can perfuse through the porous inner tube 706 and wet an inner surface of the tubing 702, in this example an inner surface of a hydrogel 714 coating the porous inner tube 706. As described for the sidewall 608, this perfusion and wetting can reduce contact, adhesion, and attachment between blood cells 712 flowing within the tubing 702 and the tubing 702 itself.

The solid outer tube 704, the porous inner tube 706, and the hydrogel 714 can have the characteristics described, respectively, for the solid outer membrane 610, the porous inner membrane 612, and the hydrogel layer 616 described in reference to FIG. 6A, and the catheter 700 can be provided with a perfusing liquid 708 as described in reference to the blood bag 600. In some implementations, the catheter 700 includes one or more ports 720 to facilitate introduction and/or pressurization of the liquid 708.

Figure 7B:
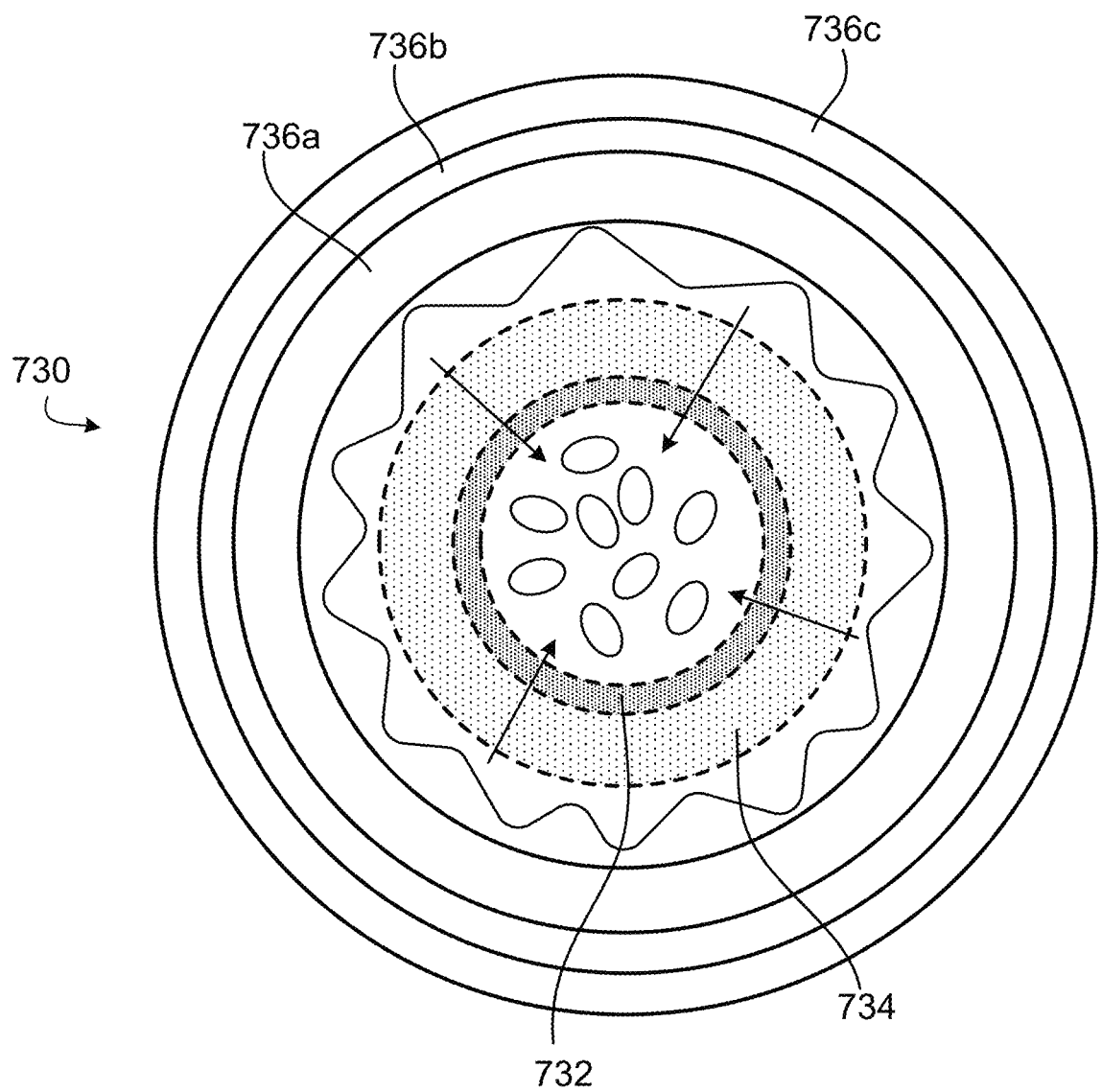

In some implementations, the tubing including a porous inner NPR tube includes more than two layers. For example, as shown in FIG. 7B, in some implementations tubing 730 includes a hydrogel layer 732, a porous NPR tube 734, and two or more solid PPR tubes 736a, 736b, 736c. The two or more solid PPR tubes 736a, 736b, 736c may together promote improved flexibility, resilience, and chemical isolation compared to tubes with single PPR outer tubes. In some implementations, one or more coaxial tubes besides the innermost tube have a negative Poisson's ratio, in addition to the inner tube.

Because of the inclusion of the inner NPR tube, tubing such as tubing 702 and tubing 730 may respond more favorably to pressures and stresses. For example, if a pressure of the liquid (e.g., blood) transported within the tubing changes unexpectedly, the inner NPR tube may compensate by shrinking/expanding (e.g., in a radial and/or axial direction) oppositely to how a PPR tube would respond. This can provide more stable liquid delivery over time and make the tubing more mechanically stable and reliable. Moreover, the porous structure of the inner NPR tube facilitates perfusion and wetting to reduce blood or other liquid damage. These benefits can be provided when the tubing is incorporated into various medical and non-medical devices, such as dialysis lines, catheters, drug provision lines, chemical analysis lines, and other devices.

Figure 7C:
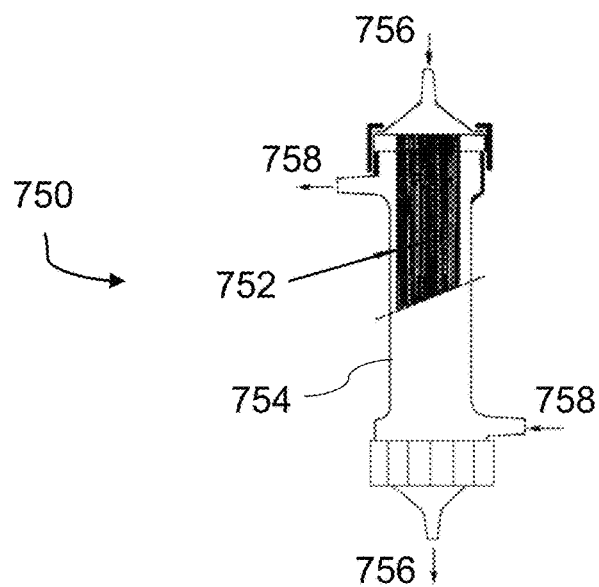
FIGS. 7C-7D are diagrams of an example dialyzer.

Besides inclusion in dialysis blood transport tubes/lines, in some implementations NPR membranes are integrated into a dialyzing module such as the dialyzing module 108 shown in FIG. 1. For example, NPR membranes can be incorporated into hollow fiber dialyzers. In a hollow fiber dialyzer 750, as shown in FIG. 7C, a fiber bundle 752 includes thousands of hollow fibers, e.g., several thousand to twenty thousand fibers, or more. Each fiber may have an internal diameter of 100 to 300 μm, or another size in some implementations, a wall thickness of 20 to 40 μm, or another size in some implementations, and a length of multiple centimeters, e.g., up to 14 cm long, or longer in some implementations. The fiber bundle 752 is encased in an enclosure 754. Blood 756 flows into the enclosure 754, through the hollow centers of the fibers of the fiber bundle 752, and out of the enclosure 754. The enclosure 754 also encases a dialysate 758 exterior to the hollow fibers, the dialysate 758 likewise flowing continuously into and out of the enclosure. Solute in the blood 756 diffuses through sidewalls of the hollow fibers and into the dialysate 758.

Figure 7D:
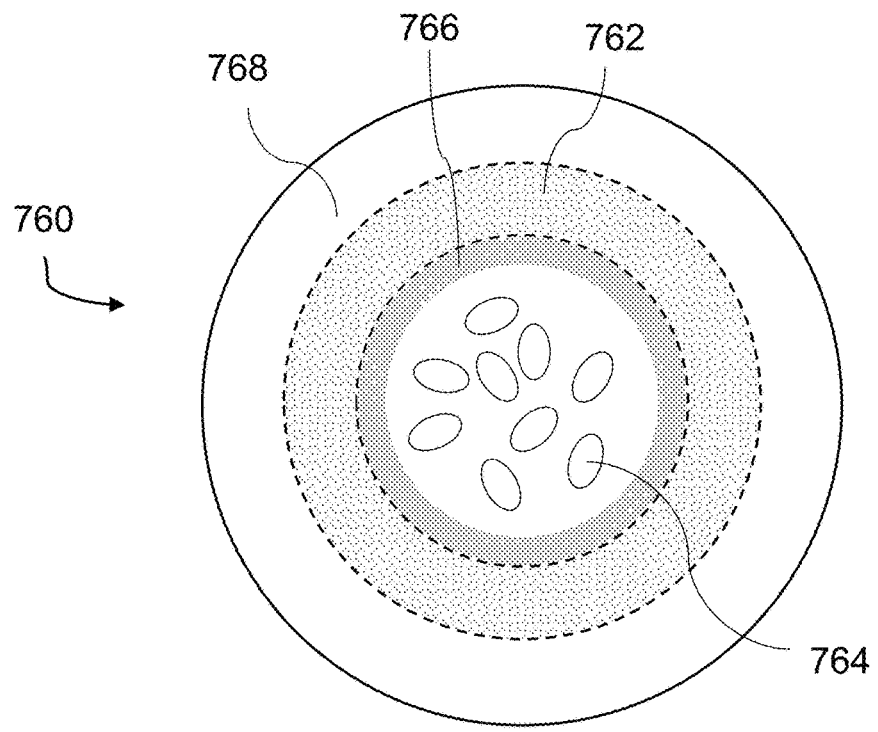

In some implementations, each hollow fiber includes an inner NPR membrane. For example, in the example of FIG. 7D, each hollow fiber 760 includes an inner NPR tube 762 enclosing blood 764 flowing in the hollow fiber 760. The inner NPR tube 762 may have any or all of the characteristics described for porous inner tube 706. Optionally, a hydrogel layer 766, as described in reference to FIGS. 6A-7B, coats an inner surface of the inner NPR tube 762. Optionally, an outer PPR tube 768 encloses the inner NPR tube 762. The outer PPR tube 768 is porous so as to allow for out-diffusion of solutes from the blood 764. In some implementations, the outer PPR tube 768 provides mechanical backing to support the inner NPR tube 762. The use of an NPR material for the inner NPR tube 762 can provide benefits such as those discussed in reference to FIGS. 6A-7B and throughout this disclosure.

In some implementations, structures including an inner porous NPR material (such as the inner porous membrane shown in FIGS. 6A-6B and the inner porous tube shown in FIGS. 7A-7B) can be combinable with one another. For example, blocks of sidewall (e.g., sidewall 608) may be attached to one another to form larger structures of whatever final shape is desired, such as a portion of a blood bag. The separate blocks may be interconnected by wetting the separate blocks and attaching them to one another, with the wetting promoting attachment. In some cases, heat and/or pressure may be applied to promote the attachment. The same methods can be used to attach portions of tubing (e.g., tubing 702) together serially to form longer tubes.

NPR portions of medical devices and implants, such as the inner porous membrane shown in FIGS. 6A-6B and the inner porous tube shown in FIGS. 7A-7B, can be produced in a variety of ways. In some implementations, an initially PPR material (sometimes referred to as a "precursor material") is converted into the NPR material. For example, a porous PPR sponge or foam can be transformed to change its structure into a structure that exhibits a negative Poisson's ratio. In some examples, NPR foams are produced by transformation of nanostructured or microstructured PPR materials, such as nanospheres, microspheres, nanotubes/ nanotubules, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layers of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. In an example, a PPR foam composed of a ductile metal can be transformed into an NPR foam by uniaxially compressing the PPR foam until the foam yields, followed by uniaxially compression in other directions.

Figure 8A:
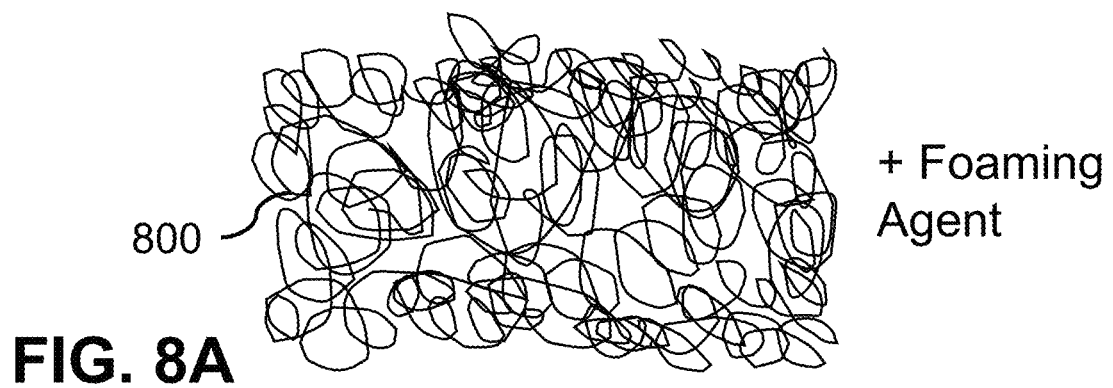
FIGS. 8A-8C are diagrams showing an example process of making an NPR material.
Figure 8B:
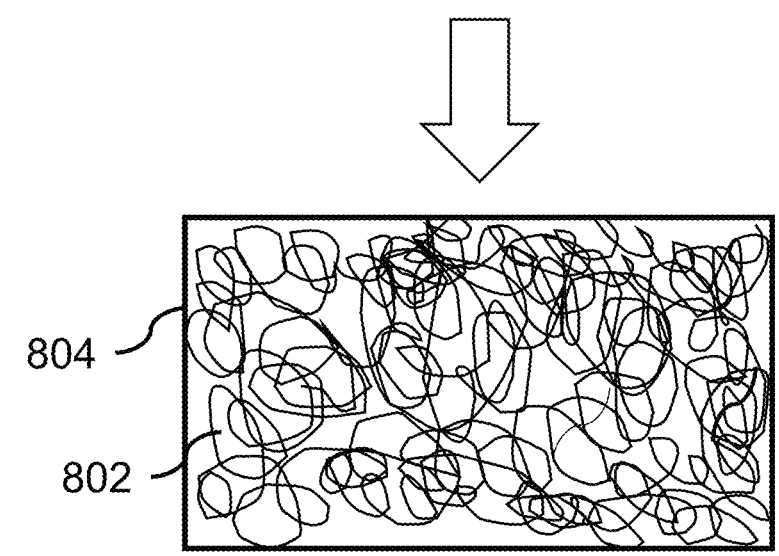
Figure 8C:
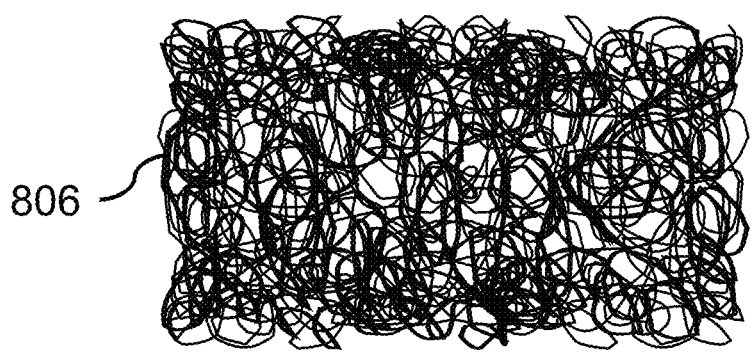

FIGS. 8A-8C illustrate an example method of making an NPR material. The NPR material may be a porous membrane, a porous tube, a porous filler material, a hydrogel, an NPR-PPR composite material, or another material in accordance with this disclosure. A granular or powdered material 800, such as a polymer material (e.g., a rubber) or a metal (e.g., stainless steel) is mixed with a foaming agent to form a porous material (e.g., a sponge or a foam) 802. The porous material 802 is placed into a mold 804. Pressure is applied to compress the porous material 802, and the compressed porous material 802 is heated to a temperature above its softening point. The compressed, heated porous material 802 is then allowed to cool, resulting in an NPR material 806. The thickness and dimensions of the mold 804 determine the resulting shape of the NPR material 806. For example, to make a porous NPR membrane, two flat plates of a mold may be moved to within tens of microns of one another. To make a porous NPR tube, the mold 804 may be annular.

Figure 9A:
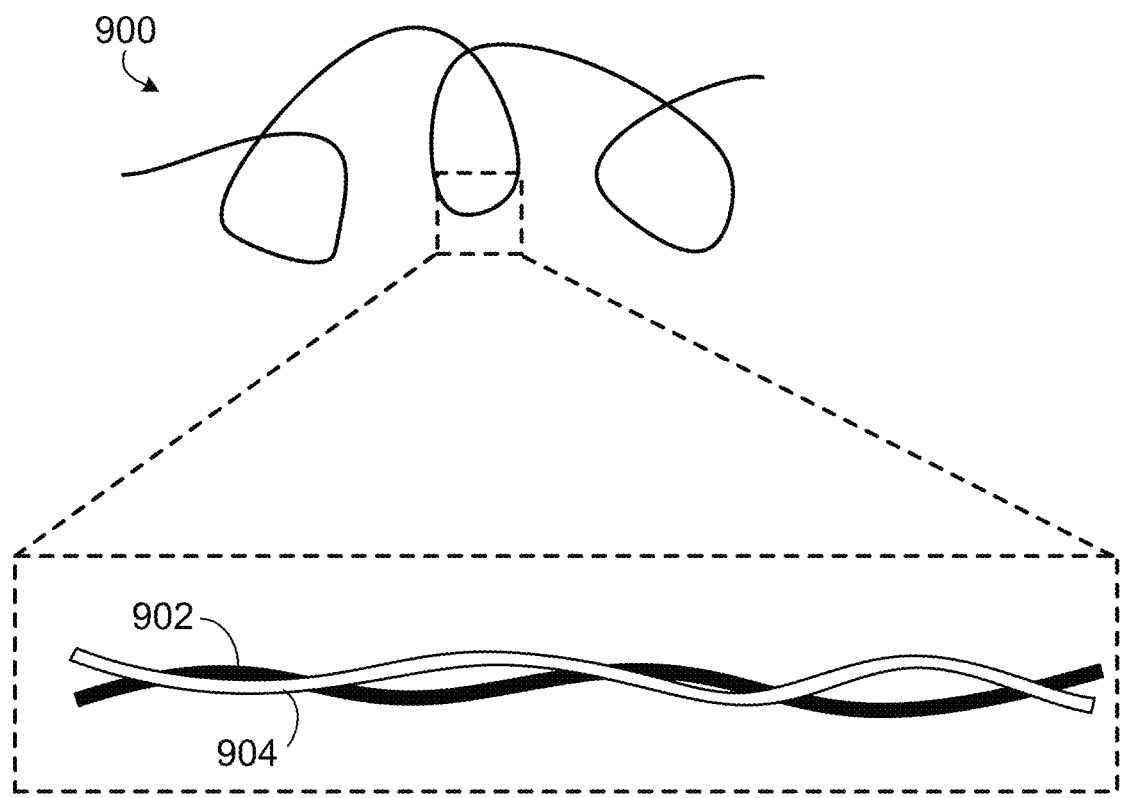
FIGS. 9A-9B are diagrams showing example sutures.

NPR materials can be integrated into sutures. For example, as shown in FIG. 9A, a suture 900 includes two filaments 902, 904 braided around one another to form the suture 900. The first filament 902 has a negative Poisson's ratio, while the second filament 904 has a positive Poisson's ratio. Some implementations according to this disclosure include more than two filaments braided around one another, e.g., between ten filaments and 100 filaments for a fine suture, between 100 filaments and 1000 filaments for a medium suture, and between 1000 filaments and 10000 filaments for a thick suture. The total diameter of the suture 900 may be between 1 µm and 1 mm, e.g., between 0.01 mm and 1 mm, or another size. In some implementations, of these filaments, at least one has a negative Poisson's ratio and at least one has a positive Poisson's ratio. However, in some implementations, each filament in a suture has a negative Poisson's ratio. Moreover, in some implementations, a suture is a "monofilament" suture that includes one NPR filament, which may or may not be combined with a PPR material.

Figure 9B:

FIG. 9B shows another example of a suture 910 including an NPR material. In this example, an inner NPR filament core 912 is coated by a PPR material 914, e.g., a PPR filament material. In some implementations, the inner NPR filament core 912 coated by the PPR material 914 represents one filament that is braided together with other filaments (e.g., other NPR/PPR filaments, other NPR filaments, and/or other PPR filaments) to form an overall suture. The coating PPR material 914 may have a variety of thicknesses depending on the diameter of the underlying inner NPR filament core 912. For example, in some implementations, the PPR material 914 has a thickness between 200 nm and 50 µm, e.g., between 500 nm and 10 µm or between 500 nm and 5 µm.

In some implementations, a filament is composed of a composite NPR-PPR material, e.g., a matrix composite.

In some implementations, to make NPR material-incorporating sutures (e.g., sutures 900, 910), an initial nanostructured PPR filament (e.g., an extruded filament) is converted into an NPR filament, e.g., by the application of heat and/or pressure in a mold, as described in reference to FIGS. 8A-8C. In some implementations, the heat and/or pressure may be applied as part of an extrusion process that defines the dimensions of the filament and forms the NPR filament from a nanostructured PPR material, e.g., nanospheres converted into a porous sponge. In some implementations, the PPR precursor structure is formed by 3D printing or another additive technique.

When an NPR filament is to be coated with PPR material (e.g., as shown in FIG. 9B), the PPR material may be applied on the NPR filament by one or more methods, including immersion, dip-coating, spray coating, vapor deposition, or another method. For suture applications, the PPR material (e.g., PPR material used as a precursor to produce NPR material, PPR material coated onto an NPR filament, or PPR material of a PPR filament braided with an NPR filament) may be a biocompatible synthetic suture material such as PGA, PLA, polyethylene, polypropylene, nylons, polyesters, or co-polymers thereof, and/or stainless steel and/or tantalum. In some implementations, NPR filaments (before and/or after braiding into a suture) are stretched during annealing in an inert atmosphere (e.g., a nitrogen atmosphere). This can increase the strength of the resulting suture.

Sutures, although widely used, can contribute to health problems in patients. For example, sutures are known to provide conduits for ingress of pathogenic microorganisms into the body. Sutures can also chemically or physically modify the body's immune response or provide an environment favorable to bacterial growth. The inclusion of NPR material in sutures, as described in this disclosure, can reduce or prevent these negative effects. For example, the NPR material-containing sutures may be lighter than equivalent PPR-only sutures, while providing equal or greater strength and durability. Stronger and lighter sutures can better maintain their grip over time and thereby prevent tissue separation and accompanying health difficulties. NPR material-containing sutures may also be more pliable than PPR-only sutures, further increasing their durability and longevity. In addition, NPR material-containing sutures may exhibit smaller diameter changes in response to changing applied forces, when compared to PPR-only sutures, because the NPR material provides a compensatory diameter-changing contribution. This may reduce damage to tissue surrounding the sutures.

NPR hydrogels can also be incorporated into medical devices and implants. For example, hydrogels can be used as filler material in medical implants, such as breast implants and joint implants (e.g., to replace cartilage in the knee); to form contact lenses; for drug delivery, e.g., for targeted diffusion-based drug delivery through a porous hydrogel; as a cellular carrier in association with stem cell differentiation for tissue regeneration; and in other applications, such as the hydrogel coating described in reference to FIGS. 6A-6B and 7A-7B. Hydrogels used in any of these applications can have a negative Poisson's ratio that provides improvements to performance and/or durability.

Figure 10A:
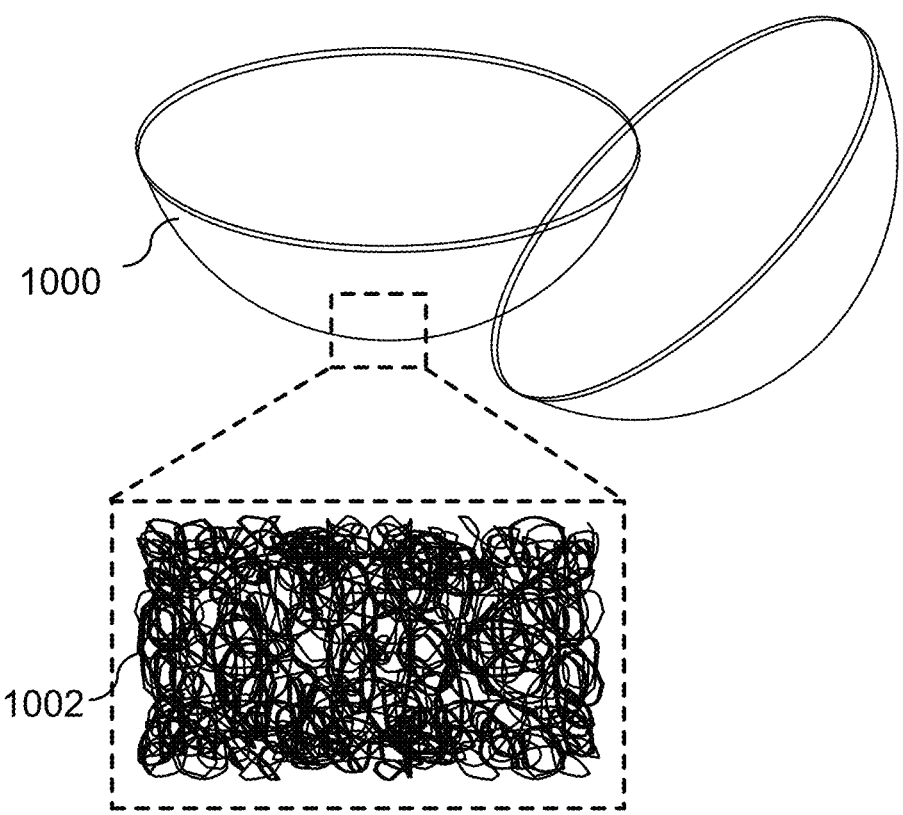
FIGS. 10A-10B are diagrams showing example NPR hydrogels.
Figure 10B:
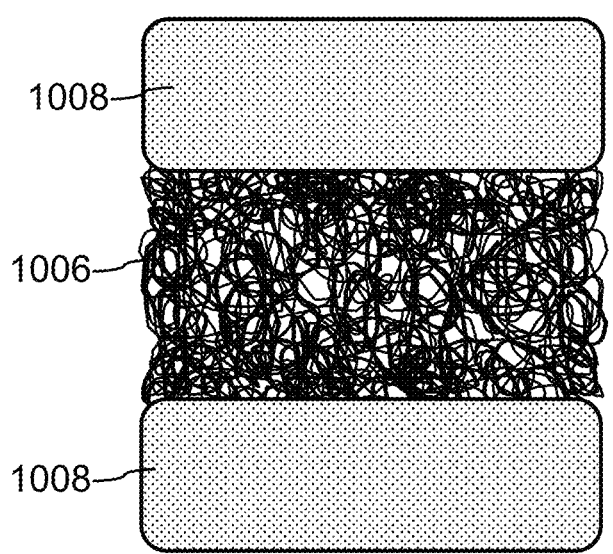

As shown in FIG. 10A, a contact lens 1000 is formed from a hydrogel 1002 having a negative Poisson's ratio. In some implementations, the contact lens 1000 is formed from a composite NPR-PPR hydrogel 1004 as shown in FIG. 10B, e.g., a structure with an inner NPR hydrogel 1006 and an outer coating or layer of PPR hydrogel 1008, either on one side of the inner NPR hydrogel 1006 or on both sides. Other NPR-PPR composite hydrogels may instead or additionally be used, e.g., matrix composites, as described in more detail above. Examples of hydrogel materials suitable for NPR or NPR-PPR structures include silicone-based hydrogels (e.g., silicone, silioxanes, fluorosiloxanes, and derivatives thereof) and pHEMA. Co-polymeric hydrogel materials may be used, e.g., methafilcon, which may improve oxygen permeability.

To form the NPR hydrogel (e.g., hydrogel 1002), a porous hydrogel structure can be formed, e.g., formed of hydrogel nanospheres. This structure can then be subjected to heat and/or pressure as described in reference to FIGS. 8A-8C, to convert the structure to a negative Poisson's ratio material.

In some implementations, the porous hydrogel structure can be formed by injection, e.g., by a lost-wax technique. Additive methods may instead or additionally be used, e.g., bioprinting. Moreover, in some implementations, the hydrogel (NPR, PPR, or NPR-PPR) is incorporated with cell and/or growth factors during or after 3D printing to generate an NPR structure with the incorporated cell and/or growth factors. In some implementations, a stereolithography apparatus or digital light processing printer is used in conjunction with a hydrogel containing a photo-sensitive resin/photoinitiator. Optical curing by light exposure causes the hydrogel to turn into a semi-solid or solid object.

In some implementations, a composite NPR-PPR hydrogel (e.g., composite NPR-PPR pHEMA, such as a laminar composite, a matrix composite, or another composite) is formed to have a fibrous shape, e.g., by extrusion or another method, such as described for NPR material-containing filaments in reference to FIGS. 9A-9B. The fibrous material can be incorporated into 3D printing processes to form medical implants such as breast implants, disk implants, hip implants, or knee implants. This process can also be used to make other types of medical devices, e.g., orthotics.

Because of the stress-response properties of NPR hydrogels, devices and implants that include the NPR hydrogels may maintain homeostasis better than devices and implants that include PPR hydrogels. For example, a PPR hydrogel included as a soft tissue substitute in an implant may, when subjected to a high pressure along a first axis, expand significantly along a second, orthogonal axis, leading to implant deformation, rupturing, damage to surrounding tissues, or other problems. NPR hydrogels shrink along the second axis rather than expand when subjected to such pressures and are therefore less likely to be damaged or cause damage to the body. For composite NPR-PPR hydrogels, the NPR can provide a compensatory stress response that helps the hydrogel maintain its intended shape, size, and structure.

Figure 11:
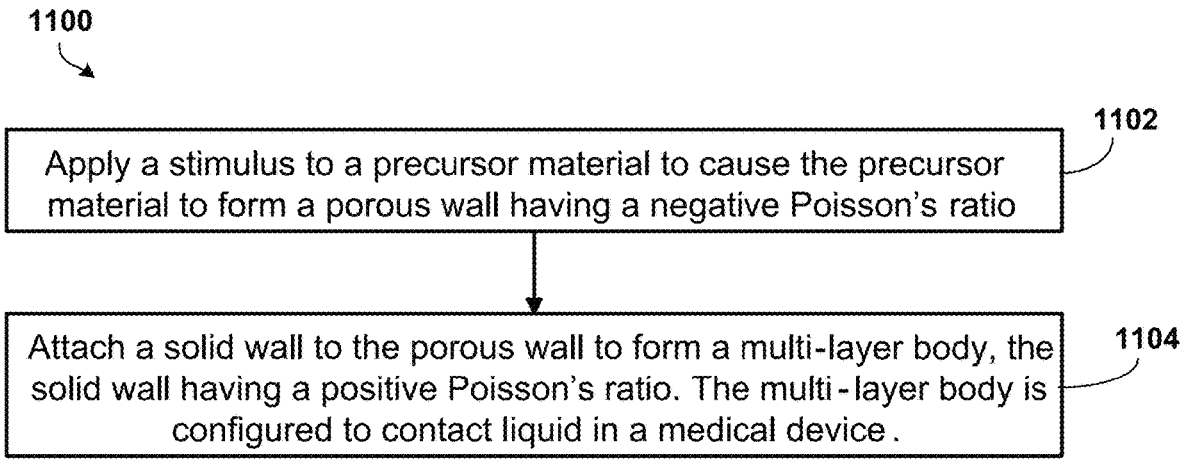
FIGS. 11-14 are diagrams showing example methods.

FIG. 11 shows an example method 1100 in accordance with this disclosure. A stimulus is applied to a precursor material to cause the precursor material to form a porous wall having a negative Poisson's ratio (1102). A solid wall is attached to the porous wall to form a multi-layer body, the solid wall having a negative Poisson's ratio (1104). The multi-layer body is configured to contact liquid in a medical device.

Figure 12:
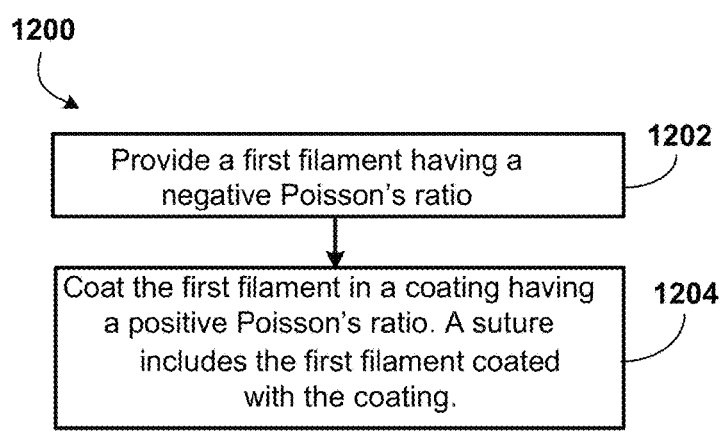

FIG. 12 shows another example method 1200 in accordance with this disclosure. A first filament is provided having a negative Poisson's ratio (1202). The first filament is coated in a coating having a positive Poisson's ratio (1204). A suture includes the first filament coated with the coating.

Figure 13:
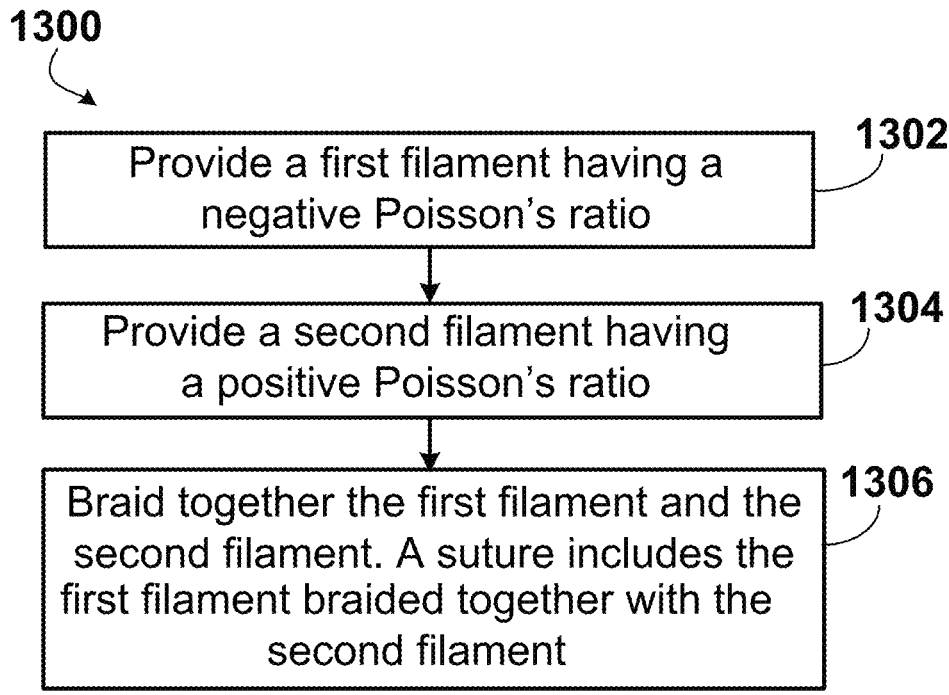

FIG. 13 shows another example method 1300 in accordance with this disclosure. A first filament is provided having a negative Poisson's ratio (1302). A second filament is provided having a positive Poisson's ratio (1304). The first filament and the second filament are braided together (1306). A suture includes the first filament braided together with the second filament.

Figure 14:
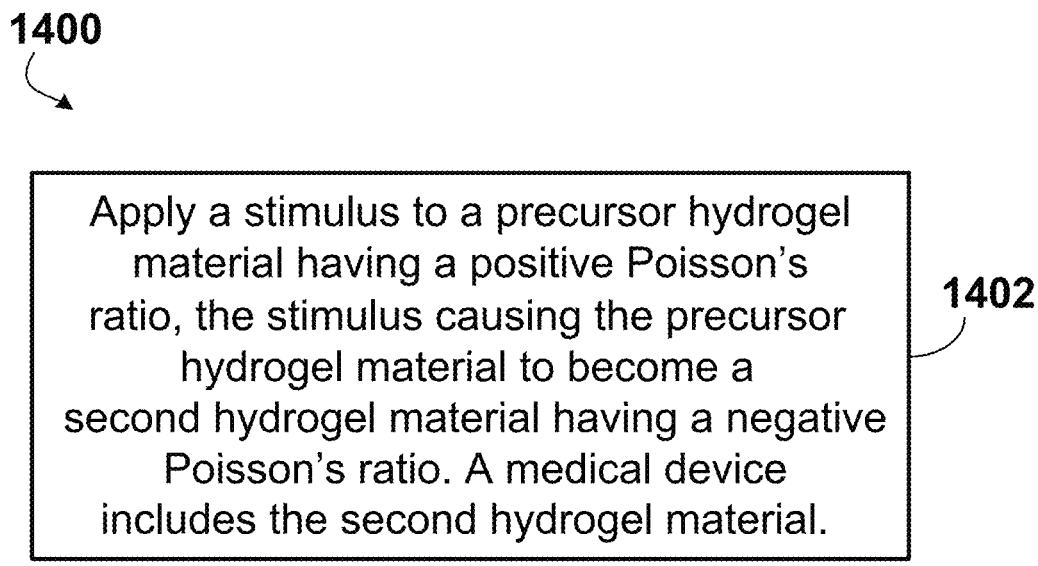

FIG. 14 shows another example method 1400 in accordance with this disclosure. A stimulus is applied to a precursor hydrogel material to having a positive Poisson's ratio (1402). The stimulus causes the precursor hydrogel material to become a second hydrogel material having a negative Poisson's ratio. A medical device includes the second hydrogel material.

Various modifications will be apparent from the foregoing detailed description. For example, structures and processes described in associated with one type of medical device or implant (e.g., a blood-contact surface, a liquid-transporting tube, a suture, or a hydrogel implant) may be equally applicable for other types of medical devices and implants. Further, features described above in connection with different implementations may, in some cases, be combined in the same implementation. In some instances, the order of the process steps may differ from that described in the particular examples above. The drawings included in this application are for illustrative purposes and are not necessarily to-scale.

Accordingly, other implementations are also within the scope of the claims.

What is claimed is:

1. A medical device comprising:
a blood bag comprising a multi-layer body defining an interior space configured to contain a liquid, the multi-layer body comprising:
a solid outer wall having a positive Poisson's ratio; and
a porous inner wall having a negative Poisson's ratio,
wherein the multi-layer body forms a wall of the blood bag.

2. The medical device of claim 1, comprising a hydrogel layer on an inner surface of the porous inner wall.

3. The medical device of claim 2, wherein the hydrogel layer has a negative Poisson's ratio.

4. The medical device of claim 1, wherein the solid outer wall and the porous inner wall are arranged to permit perfusion of a second liquid from between the solid outer wall and the porous inner wall through the porous inner wall into the interior space.

5. The medical device of claim 4, comprising a port through which the second liquid can be introduced to perfuse through the porous inner wall into the interior space.

6. The medical device of claim 1, wherein the liquid comprises blood.

7. The medical device of claim 1, wherein the porous inner wall has an interconnected porous structure.

8. The medical device of claim 1, wherein the multi-layer body comprises a plurality of solid outer walls, each of the plurality of solid outer walls having a positive Poisson's ratio.

9. The medical device of claim 1, wherein each of the porous inner wall and the solid outer wall has a thickness between 1 µm and 100 µm.

10. A method of making blood bag comprising a multi-layer body, the method comprising:
applying a stimulus to a precursor material to cause the precursor material to form a porous wall having a negative Poisson's ratio; and
attaching a solid wall to the porous wall to form the multi-layer body, the solid wall having a positive Poisson's ratio,
wherein the multi-layer body defines an interior space configured to contain a liquid, wherein the solid wall is an outer wall and the porous wall is an inner wall with respect to the interior space, and
wherein the multi-layer body forms a wall of the blood bag.

11. The method of claim 10, wherein the stimulus comprises at least one of heat or pressure.

12. The method of claim 10, comprising applying a hydrogel on a first surface of the porous wall, wherein the first surface is opposite a second surface of the porous wall to which the solid wall is attached.

13. The method of claim 12, wherein the hydrogel has a negative Poisson's ratio.

14. The method of claim 10, wherein each of the porous wall and the solid wall has a thickness between 1 µm and 100 µm.

15. The method of claim 10, wherein the solid wall and the porous wall are arranged to permit perfusion of a second liquid from between the solid wall and the porous wall through the porous wall.

* * * * *